United States Patent [19]

Miller et al.

[11] 4,060,545
[45] Nov. 29, 1977

[54] PREPARATION OF UNSATURATED CARBOXYLIC ESTERS FROM PROPYLENE OR ISOBUTYLENE

[75] Inventors: Arthur F. Miller, Lyndhurst; Robert J. Zagata, Seven Hills; Robert K. Grasselli, Chagrin Falls, all of Ohio

[73] Assignee: The Standard Oil Company, Cleveland, Ohio

[21] Appl. No.: 691,052

[22] Filed: May 28, 1976

[51] Int. Cl.$^2$ ............................................. C07C 69/54
[52] U.S. Cl. .............................. 560/208; 260/533 N; 260/604 HF; 560/131
[58] Field of Search .................................... 260/486 R

[56] References Cited

U.S. PATENT DOCUMENTS 3,293,290  12/1966  Flint ................................. 260/486 R

*Primary Examiner*—Paul J. Killos
*Attorney, Agent, or Firm*—D. J. Untener; H. D. Knudsen; L. W. Evans

[57] ABSTRACT

The production of acrylates and methacrylates, made by the oxidative esterification of propylene or isobutylene wherein gaseous reactants are contacted with one or more catalysts and ethylene or an alcohol can be advantageously conducted in a single fluid bed reactor to obtain the desired ester.

11 Claims, No Drawings

PREPARATION OF UNSATURATED CARBOXYLIC ESTERS FROM PROPYLENE OR ISOBUTYLENE

BACKGROUND OF THE INVENTION

The preparation of unsaturated carboxylic esters such as methyl methacrylate or methyl acrylate from isobutylene or propylene is known in the art. U.S. Pat. No. 3,325,534 discloses such a method wherein the unsaturated nitrile is reacted with water and an oxyacid such as sulfuric acid to form a unsaturated carboxylic acid. This acid is then esterified with an alcohol. A major disadvantage with these processes however, is that they require a plurality of reactors, one reactor to convert the olefin to an aldehyde, one to convert the aldehyde to acid, and one to convert the acid to its corresponding ester.

Direct oxidation of propylene or isobutylene to an aldehyde is well known in the art. See U.S. Pat. Nos. 3,264,225 and 3,387,038. The latter two reactants, conversion of an aldehyde to an acid and an acid to an ester have been combined into one step. See for example, U.S. Pat. No. 3,819,685 showing the preparation of esters from unsaturated aldehydes and alcohols.

The present invention carries the formation of esters one step further by combining all three reactions in a single fluid bed reactor, thereby greatly reducing the cost and complexity of producing these esters.

SUMMARY OF THE INVENTION

The invention is a process for the oxidative esterification of unsaturated olefins selected from the group consisting of propylene and isobutylene, to produce acrylates or methacrylates respectively, comprising:

a. passing a gaseous stream comprising the olefin, molecular oxygen and ethylene or an alcohol to a single fluid bed reactor, said reactor containing one or more oxidation catalysts and operated at a temperature between 200° to 600° C. and b. collecting the acrylates or methacrylates in the reactor effluent.

The invention can be advantageously utilized for the production of esters. Specifically, these esters include but are not limited to methyl acrylate from propylene and methanol and methyl methacrylate from isobutylene and methanol.

In addition to these esters, other esters may be formed through this invention by varying the type of alcohol introduced into the reactor. The preferred alcohol is methanol; however, other alcohols such as ethyl, propyl, isopropyl, butyl, isobutyl, and phenol may be used. Ethylene may also be used in place of ethyl alcohol.

In its preferred aspect, the process comprises contacting a mixture comprising propylene or isobutylene, oxygen, and ethylene or an alcohol with a catalyst at an elavated temperature. In addition, the feed may contain reactants or diluents such as steam, $CO_2$ or $N_2$ to improve the reaction.

Any source of oxygen may be employed in this process. For economic reasons, however, it is preferred that air be the source of oxygen.

The ethylene or alcohol may be added to the gaseous stream of hydrocarbon and molecular oxygen before entering the reactor, or it may be separately introduced to the reactor at a point above which the gaseous stream enters the reactor.

By preparing the ester in a single step and obtaining high yields, the cost of producing the esters are greatly reduced due to the elimination of one or more reactors. Also, the formation of the ester in one reactor assists in the desorption and volatility of the intermediate acid. In addition, other advantages such as closer temperature control of the reaction and the use of split feeds to the reactor may be realized when conducting the overall reaction in a single fluid bed reactor.

Another aspect of the invention is the catalyst employed in the fluid bed reactor. Broadly, any catalyst or combination of catalysts known in the art to produce unsaturated aldehydes or carboxylic acids from olefins through oxidation can be used in the invention.

These oxidation catalysts are well known in the art. For example, U.S. Pat. No. 3,859,358 shows a vapor phase oxidation process utilizing catalysts comprising the oxides of uranium and molybdenum. Similarly, U.S. Pat. Nos. 2,941,007, 3,328,315, 3,338,952 and 3,200,081 disclose vapor phase oxidation processes utilizing bismuth molybdate and bismuth phospholybdate catalysts, and antimony oxide in combination with oxides or uranium, iron, or manganese. U.S. Pat. No. 3,171,859 describes a process for producing unsaturated aldehydes in the presence of a catalyst comprising the oxides of iron, bismuth, phosphorus and molybdenum. U.S. Pat. No. 3,642,930 discloses a catalyst for the oxidation of olefins to aldehydes and acids comprising an alkali metal, bismuth, iron and molybdenum.

The invention contemplate one or more catalysts that perform the mentioned oxidation reactions be present in the fluidized state in the reactor.

The preferred number of catalysts is two. For example, in the process of methacrylate ester, one catalyst suited for the oxidation of isobutylene to methacrolein and one suited for the conversion of methacrolein to methacrylic acid may be used.

Some of the above catalysts are useful for both oxidation of an olefin to an aldehyde and the oxidation of an aldehyde to its corresponding ester. However, better yields have been obtained with catalysts specifically directed to each reaction.

Preferred when using two catalysts is a first oxidation catalyst of the empirical formula:

$$A_aB_bC_cD_dE_eMo_{12}O_x$$

wherein A is an alkali metal, alkaline earth metal, rare earth metal, Tl, Sm, Cu, or mixture thereof;
B is Co, Ni, Mn, Zn, Cd, Mg or mixtures thereof;
C is Ge, W, P, Sn, Sb, B, V or mixtures thereof
D is Fe, Cr, Ce or mixture thereof;
E is Bi and/or Te;
wherein $a$ is a number from 0 – 3;
$b$, $c$ and $d$ are numbers from 0 – 12;
$e$ is a number from 0.01 – 12, and
$x$ is a number determined by the valence requirements of the other elements present,
and a second oxidation catalyst of the empirical formula:

$$A_aB_bV_cMo_{12}O_x$$

wherein A is an alkali metal, alkaline earth metal, Bi, or mixture thereof;
B is P, B, Fe, Mn, U, Ce, Ge, Nb, Co, Ni, Sn, Sb, As, Cr, W or mixture thereof;
wherein $a$ is a number from 0 – 2, b and c are numbers from 0 – 12, and x is a number determined by the valence requirements of the other elements present.

When using two or more catalysts, they may be in the form of a physical blend of the several catalysts in microspheroidal form, or may be composited in a common microsphere.

The particle size or density of the catalysts may also be varied so that the first catalyst will have a tendency to be concentrated at the reactor inlet while the second catalyst will be concentrated at the reactor outlet, with a blend of the several catalysts throughout the central portion of the reactor. The mixture of these catalysts should be in a range of 1 to 99 weight percent of each catalyst. Where two catalysts are used, the preferred range is 60-95 percent of the first catalyst and 5-40 weight percent of the second catalyst.

The reactor must be of the type suitable for using a fluidized bed of catalysts. The fluid reactor may comprise an open column, or may contain a plurality of perforated trays stacked horizontally throughout the length of the column, or may be of the type using packed fluid beds. Fluidized bed reactors normally consist of a reaction zone and a disengaging zone. The disengaging zone, by itself or with the use of cyclones, recovers the catalyst from the fluidizing gas and returns it to the reactor zone. Where two or more catalysts are used, this cyclone return may be introduced at any point within the reactor.

The operating conditions of the fluidized reactor are similar to those used in the separate reactor systems. The reactor perssure can be 0 to 50 psig, perferably 0-20 psig, and the reactor temperature can be 200° to 600° C, with a preferred range of 240° to 400° C.

Contact time can range from 2 to 20 seconds, with 3 to 10 seconds preferred.

SPECIFIC EMBODIMENT

Example 1 — Esterification of isobutylene to methyl methacrylate

A fluidized bed stainless steel reactor 1½ inches in diameter and having a two foot reaction zone was charged with a blend of known catalyst consisting of 80 weight percent of a first catalyst of the formula 50% [$Ni_{2.5} Co_{4.5} Fe_3 Bi P_{0.5} K_{0.1} Mo_{12} O_x$] . 50% $SiO_2$ and 20 weight percent of a second catalyst of the formula 62% [$V_3 W_{1.2} Mo_{12} O_x$] . 38% $SiO_2$.

A feed gas was prepared containing air/isobutylene/methanol in a mole percent of 10/1/2. The reactor was run at a temperature of 355° C, and atmospheric pressure. The apparent contact time was 5 seconds. The result of this reaction is shown in Table I. The results are based on per pass conversion of isobutylene.

TABLE I

| Esterification of Isobutylene | |
|---|---|
| Product | Mole percent |
| Methyl methacrylate | 30.0 |
| Unreacted isobutylene | 53.0 |
| Acrolein | 1.0 |
| Methacrolein | 2.0 |
| Methacrylic acid | Trace |

Example 2 — Esterification of propylene to methyl acrylate

A fluidized bed stainless steel reactor 1½ inches in diameter and having a two foot reaction zone was charged with catalysts of the same composition as Example 1, but the weight percent was 75% of the first catalyst and 25% of the second catalyst. A feed gas was prepared containing air/propylene/methanol/water in a mole percent of 10/1/2/6. The reactor temperature was 260° C, at a pressure of 12 psig. The apparent contact time was 3.6 seconds. The results of this reaction is shown in Table II. The results are based on per pass conversion of propylene.

TABLE II

| Esterification of Propylene | |
|---|---|
| Product | Mole percent |
| Methyl acrylate | 29.5 |
| Unreacted propylene | 4.4 |
| Acrolein | 30.6 |
| Acrylic acid | 29.1 |

We claim:

1. A process for the oxidative esterification of unsaturated olefins selected from the group consisting of propylene and isobutylene, to produce acrylates and methacrylates, respectfully, comprising:
   a. passing a gaseous stream comprising the olefin, molecular oxygen and ethylene or an alcohol to a single fluid bed reactor, said reactor containing one or more oxidation catalysts effective for the oxidation of the olefin to its corresponding aldehyde and acid, and operated at a temperature between 200° to 600° C., and
   b. collecting the acrylates or methacrylates in the reactor effluent.

2. The process of claim 1 wherein the alcohol is selected from the group consisting of methanol, ethanol, propanol, and phenol.

3. The process of claim 1 wherein the alcohol is added to the reactor at a point above which the gaseous stream of olefin and molecular oxygen enters the reactor.

4. The process of claim 1 wherein the number of oxidation catalysts is two, the first being one that is especially effective for oxidation of the olefin to an aldehyde, the second catalyst being one that is especially effective for the oxidation of the aldehyde to its acid, in a range of from 1 to 99 weight percent of each catalyst.

5. The process of claim 4 wherein the oxidation catalyst is a mixture comprising 60 to 95 weight percent of the first catalyst and 5 to 40 weight percent of the second catalyst.

6. The process of claim 4 wherein the first oxidation catalyst is described by the empirical formula:

$$A_aB_bC_cD_dE_eMo_{12}O_x$$

wherein A is an alkali metal, alkaline earth metal, rare earth metal, Tl, Sm, Cu, or mixture thereof;
B is Co, Ni, Mn, Zn, Cd, Mg, or mixture thereof;
C is Ge, W, P, Sn, Sb, B, V, or mixture thereof;
D is Fe, Cr and/or Ce
E is Bi and/or Te
wherein a is a number from 0 – 3,
b, c and d are numbers from 0 – 12,
e is a number from 0.01 – 12, and
x is a number determined by the valence requirements of the other elements present.

7. The process of claim 4 wherein the second oxidation catalyst is described by the empirical formula:

$$A_aB_bV_cMo_{12}O_x$$

herein A is an alkali metal, alkaline earth metal, Bi, or mixture thereof;

B is P, B, Fe, Mn, U, Ce, Ge, Nb, Co, Ni, Sn, Sb, As, Cr, W or mixture thereof;

wherein A is a number from 0 – 2, $b$ and $c$ are numbers from 0 – 12, and $x$ is a number determined by the valence requirements of the other elements present.

8. The process of claim 4 wherein the olefin is isobutylene.

9. The process of claim 8 wherein the alcohol is methanol, and the ester formed is methyl methacrylate.

10. The process of claim 4 wherein the olefin is propylene.

11. The process of claim 10 wherein the alcohol is methanol, and the ester formed is methyl acrylate.